United States Patent [19]

Miwa et al.

[11] Patent Number: 5,772,588
[45] Date of Patent: Jun. 30, 1998

[54] APPARATUS AND METHOD FOR MEASURING A SCATTERING MEDIUM

[75] Inventors: Mitsuharu Miwa; Yutaka Tsuchiya, both of Hamamatsu, Japan

[73] Assignee: Hamamatsu Photonics K.K., Shizuoka-ken, Japan

[21] Appl. No.: 704,124

[22] Filed: Aug. 28, 1996

[30] Foreign Application Priority Data

Aug. 29, 1995 [JP] Japan ..................................... 7-220493

[51] Int. Cl.[6] ...................................................... A61B 3/00
[52] U.S. Cl. ........................... 600/310; 600/323; 600/473
[58] Field of Search ..................................... 128/633, 664, 128/665; 600/310, 322, 323, 326, 328, 473, 476

[56] References Cited

U.S. PATENT DOCUMENTS

| 5,119,815 | 6/1992 | Chance . | |
|---|---|---|---|
| 5,386,827 | 2/1995 | Chance et al. . | |
| 5,413,098 | 5/1995 | Benaron | 128/633 |
| 5,503,148 | 4/1996 | Pologe et al. | 128/633 |
| 5,582,169 | 12/1996 | Oda et al. | 128/633 |

OTHER PUBLICATIONS

Time Resolved Reflectance and Transmittance for the Non-Invasive Measurement of Tissue Optical Properties, M.S.Patterson et al,Jun.15, 1989/vol.28,No.12/Applied Optics, pp. 2331–2336 (See Appln. p. 14).

Analytical Biochemistry 195, 330–351 (1991) Quantitation of Time–and Frequency–Resolved Optical Spectra for the Determination of Tissue Oxygenation. E.M.Sevick et al. pp. 330–351 (See also Appln. p. 19).

Primary Examiner—Jennifer Bahr
Assistant Examiner—Eric F. Winakur
Attorney, Agent, or Firm—Cushman Darby & Cushman IP Group of Pillsbury Madison & Sutro, LLP

[57] ABSTRACT

An apparatus and method are provided for measuring a scattering medium containing a light absorbing substance. The apparatus includes a light source; a photodetector; a gate voltage applying circuit for applying gate voltage pulses to the photodetector at a plurality of detection timings in order to generate the photodetector output light detection signals corresponding to the intensity of the light during periods of application of the pulses; and a signal processing unit for obtaining signal intensities during the periods and calculating internal information of the scattering medium based on the signal intensities.

24 Claims, 9 Drawing Sheets

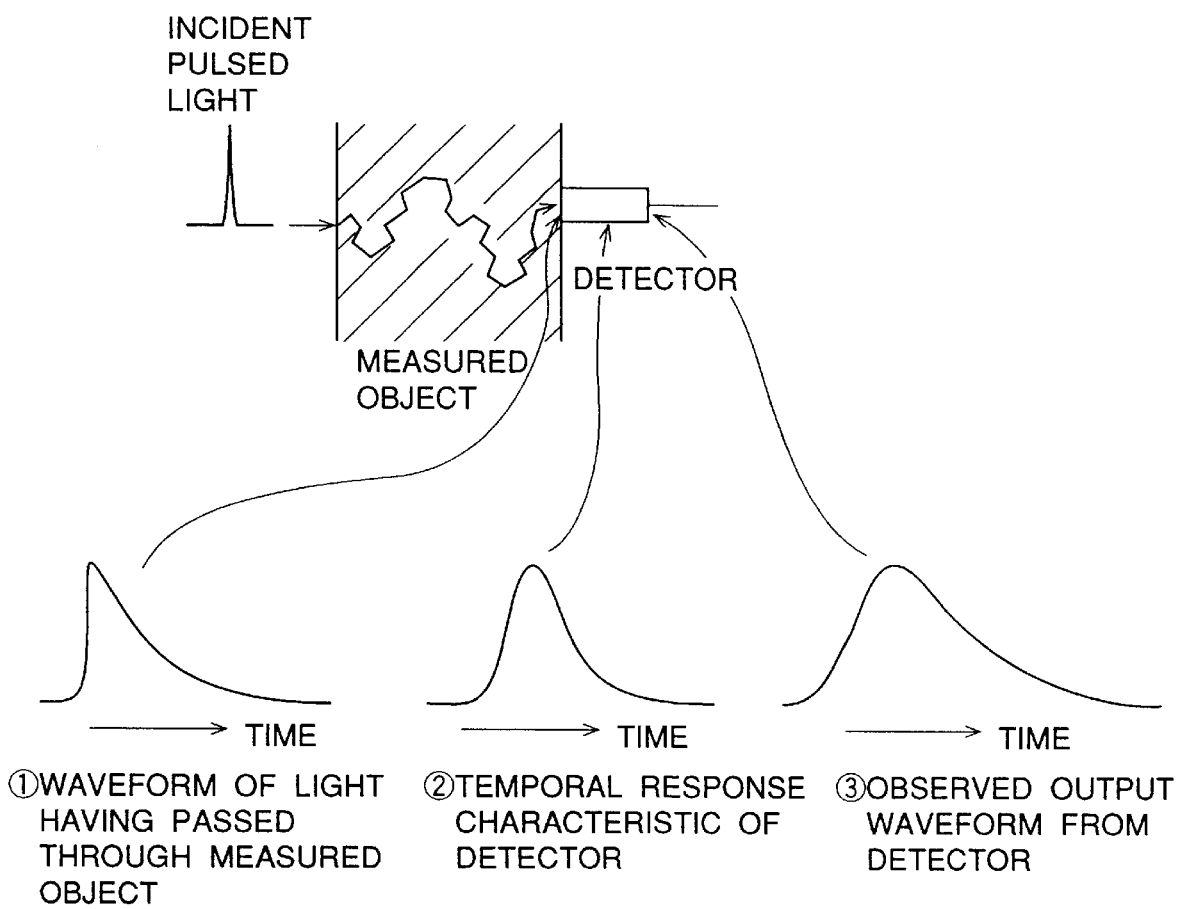

TRANSMISSION TYPE

REFLECTION TYPE

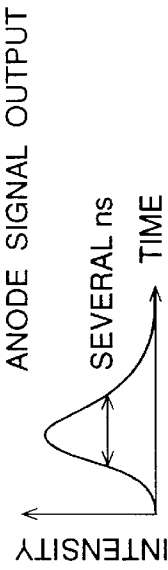
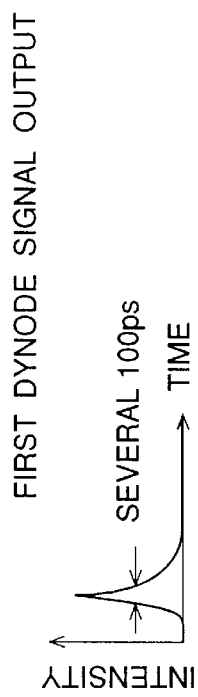
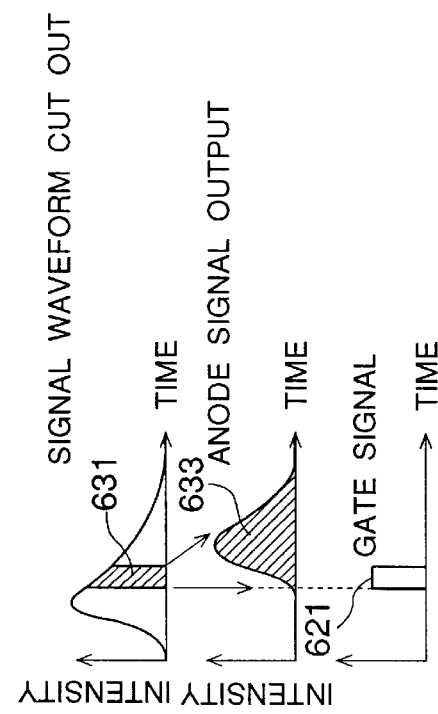
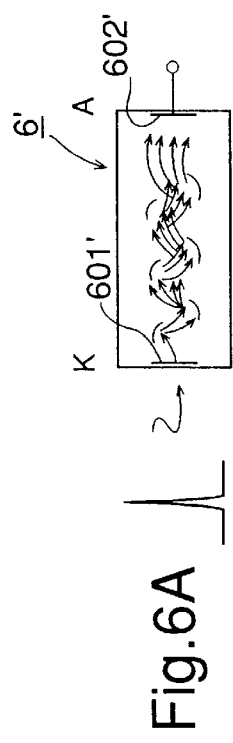
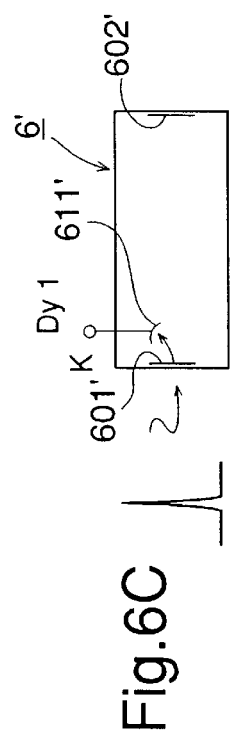
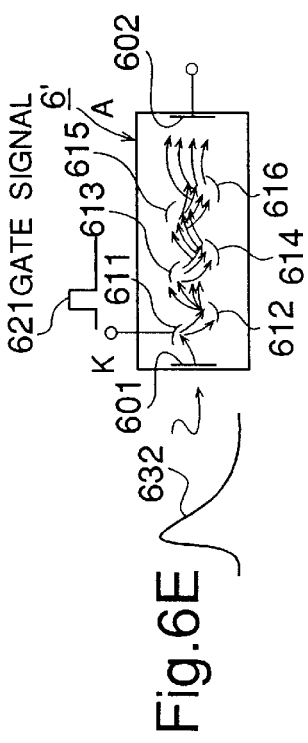

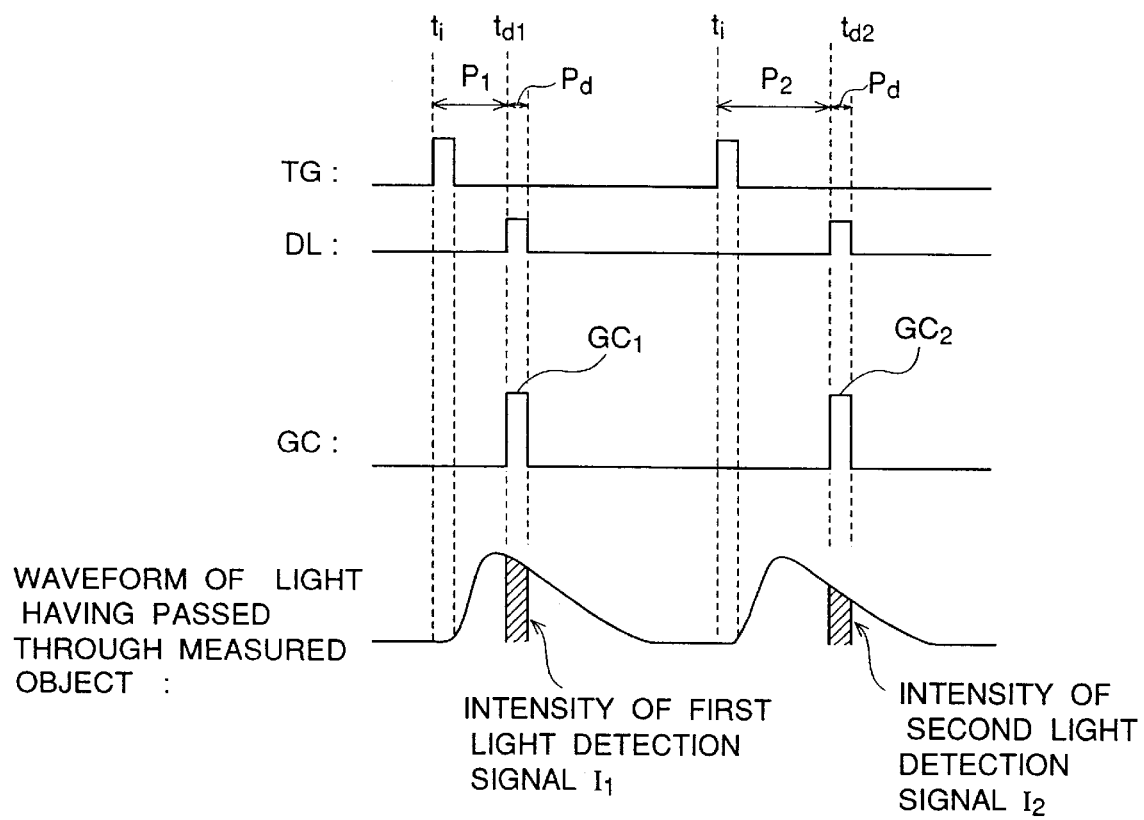

APPARATUS AND METHOD FOR MEASURING A SCATTERING MEDIUM

BACKGROUND OF THE INVENTION

1. Field of the Invention

The present invention relates to an apparatus and method for measuring a scattering medium. More specifically, the present invention relates to an apparatus and method for measuring a concentration of a light absorbing substance in a scattering medium.

2. Related Background Art

Time-resolved spectroscopy was proposed as a technique for quantitatively measuring a concentration of an absorbing substance in a scattering medium (for example, in U.S. Pat. No. 5,119,815). By this technique, when a light pulse is incident to the scattering medium such as a living body, a temporally spread profile of light pulse is observed because of the scattering inside a living tissue, thus obtaining a profile indicating a change of light intensity against a change of time. A concentration of absorption inside the living tissue can be attained by taking a logarithm of the light intensity of the thus obtained profile and obtaining the slope of the light intensity with respect to the time.

The above-described technique usually employs the time-resolved single-photoelectron measuring method. In the time-resolved single-photoelectron measuring method, the quantity of light detected for each incident light pulse is limited to only one photon. Namely, when a light pulse incident to living tissue in a scattering medium travels through the inside of the living tissue so as to cause a substantial amount of light to reach a detector, the measuring method has a drawback in that a substantial amount of time is necessary for data acquisition, because the light must be detected as photons. In addition, the apparatus used in the time-resolved single-photoelectron measuring method is expensive, and, therefore, fields of application thereof are limited to some extent.

B. Chance and K. Kaufmann proposed an apparatus using a boxcar integrator as means for solving the above problems (U.S. Pat. No. 5,386,827). This technique is arranged to let temporally very short pulsed light enter a scattering medium such as a living body, to detect light of a predetermined wavelength appearing on a surface after diffuse propagation inside the scattering medium by means of a detector, to guide a signal output from the detector to the boxcar integrator, and to calculate an absorption coefficient from signals at two or more predetermined timings corresponding to an attenuation slope of the signal output from the detector by means of the boxcar integrator.

By obtaining absorption coefficients with respect to two different wavelengths by the above technique, a concentration of a specific absorptive constituent, for example hemoglobin or the like, in a scattering medium such as a living body is quantified based on the information of these two absorption coefficients. Since this technique is free from the limitation of a single photon of light, it enables a short-time measurement if a quantity of light reaching the detector is sufficiently large. It also enables a reduction of cost of the apparatus.

However, the above technique using the boxcar integrator has a problem in that the absorption coefficient cannot be measured accurately, because a temporal response characteristic of the detector is superimposed on a true waveform so as to dull the waveform. FIG. 1 is an explanatory drawing of the waveform dullness, which schematically shows pulsed light having passed through a measured object, the temporal response characteristic of detector, and an output waveform from the detector as observed. It is known that because of the waveform dullness, for example, when a living body is irradiated with temporally very short pulsed light, the half-width of the transmitted light is approximately 5 ns. In regards to a photomultiplier tube as an example of the detector for measuring the transmitted light, the temporal response characteristic of the photomultiplier tube is approximately 3 to 5 ns because of dispersion in the migration time of electrons in the photomultiplier tube, and a signal output observed is largely affected by the temporal response characteristic of the photomultiplier tube.

SUMMARY OF THE INVENTION

The present invention has been developed to work under the above circumstances. An object of the present invention is to provide an apparatus for measuring internal information, such as a concentration of an absorptive substance, in the scattering medium at high accuracy and on a noninvasive basis. Another object of the present invention is to provide a method for measuring internal information, such as a concentration of an absorptive substance, in the scattering medium at high accuracy and on a noninvasive basis.

The apparatus of the present invention is used for measuring a scattering medium containing a light absorbing substance, and the apparatus comprises:

(a) a light source for emitting light of a predetermined wavelength, the light being incident on the scattering medium at an incident timing;

(b) a photodetector for detecting intensity of the light which has diffusely propagated through the scattering medium from an incident position to a detection position;

(c) a gate voltage applying circuit for applying gate voltage pulses to said photodetector at a plurality of detection timings, the periods between the incident timing and the detection timings being different from each other, in order to make the photodetector output light detection signals correspond to the intensity of the light during periods of application of the gate voltage pulses; and (d) a signal processing unit for collecting the light detection signals to obtain signal intensities during the periods of application of the gate voltage pulses, and calculating internal information of the scattering medium based on the signal intensities thus obtained.

The predetermined wavelength of the light emitted by the light source according to the present invention is preferably not less than 600 nm and not more than 1500 nm. Further, the light to be incident on the scattering medium is preferably pulsed light.

The photodetector according to the present invention preferably has a gating circuit which is connected to the gate voltage applying circuit. Further, a photomultiplier tube having a dynode which is connected to said gate voltage applying circuit is more preferably used as the photodetector according to the present invention. The photodetector may detect intensity of the light at a plurality of detection positions on the surface of the scattering medium.

The apparatus of the present invention preferably further comprises a timing controller for controlling the detection timings when the gate voltage pulses are generated by the gate voltage applying circuit and the incident timing when the light is emitted by the light source.

The present apparatus may further comprise an integrator for integrating the signal intensities during the periods of application of the gate voltage pulses, respectively.

In the apparatus of the present invention, the signal processing unit may be arranged to obtain a temporal slope of intensity of the light which has diffusely propagated through the scattering medium, based on the signal intensities during the periods of application of the gate voltage pulses, and then to calculate, as the internal information, an absorption coefficient in the scattering medium and a concentration of the absorbing substance based on the temporal slope.

In a case where the scattering medium to be measured contains a plurality of light absorbing substances, it is preferable that the light according to the present invention have a plurality of predetermined wavelengths, and the signal processing unit is arranged to calculate absorption coefficients with respect to the wavelengths and to calculate concentrations of the light absorbing substances based on the absorption coefficients.

When the scattering medium contains oxygenated hemoglobin and deoxygenated hemoglobin as the light absorbing substance, the signal processing unit can be arranged to calculate a concentration of the oxygenated hemoglobin, a concentration of the deoxygenated hemoglobin and an oxygen saturation of hemoglobin as the internal information.

The method for measuring a scattering medium of the present invention comprises the steps of:

(i) emitting light of a predetermined wavelength from a light source, the light being to be incident on the scattering medium at an incident timing;

(ii) detecting intensity of the light by a photodetector, the light having been diffusely propagated through the scattering medium from an incident position to a detection position;

(iii) applying gate voltage pulses to the photodetector at a plurality of detection timings by a gate voltage applying circuit, periods between the incident timing and the detection timings being different from each other, in order to make the photodetector output light detection signals corresponding to intensity of the light during periods of application of the gate voltage pulses; and (iv) collecting the light detection signals by a signal processing unit to obtain signal intensities during the periods of application of the gate voltage pulses, and calculating internal information of the scattering medium based on the signal intensities thus obtained.

The method of the present invention preferably further comprises the step of controlling the detection timings when the gate voltage pulses are generated and the incident timing when the light is emitted.

The present method may further comprise the step of integrating said signal intensities during the periods of application of said gate voltage pulses, respectively.

The method of the present invention may further comprise the steps of obtaining a temporal slope of intensity of the light which has diffusely propagated through the scattering medium, based on the signal intensities during the periods of application of the gate voltage pulses, and calculating, as the internal information, an absorption coefficient in the scattering medium and a concentration of the absorbing substance based on the temporal slope.

In a case where the scattering medium to be measured contains a plurality of light absorbing substances, it is preferable that the light according to the present invention have a plurality of predetermined wavelengths, and the present method further comprises the steps of calculating absorption coefficients with respect to the wavelengths and calculating concentrations of the light absorbing substances based on the absorption coefficients.

When the scattering medium contains oxygenated hemoglobin and deoxygenated hemoglobin as the light absorbing substance, the present method can further comprise the step of calculating a concentration of the oxygenated hemoglobin, a concentration of the deoxygenated hemoglobin and an oxygen saturation of hemoglobin as the internal information.

In the apparatus and the method of the present invention, the gate voltage pulses are applied to the photodetector in order to detect the intensity of light which has passed through the scattering medium, at different timings synchronized with the transmitted light. According to the apparatus and the method of the present invention, therefore, internal information of the scattering medium, such as an absorption coefficient with respect to the light and a concentration of a light absorbing substance, can be measured with good accuracy without influence of the temporal response characteristic of the photodetector.

According to the apparatus and the method of the present invention, it becomes possible to obtain, with good accuracy, absorption coefficients with respect to the light having two or more different wavelengths and, thus, to quantitatively measure with good accuracy from the information of these two or more absorption coefficients for a specific absorptive constituent in the scattering medium such as the living body, for example, for hemoglobin or the like.

As mentioned above, in the apparatus and the method of the present invention, the temporal response characteristic of the light having passed through the scattering medium, mainly the attenuation rate (attenuation property) of the light, can be accurately obtained without being affected by the temporal response characteristic of the photodetector and, thereby, internal information of the scattering medium, such as a concentration of an absorptive substance, can be measured with good accuracy. The present invention is free of the necessity to reduce the light quantity to one photon or less, even if the quantity of the light reaching the photodetector is sufficiently large, and permits data acquisition within a short period of time. Further, because the apparatus and the method of the present invention are relatively simple, a cheap apparatus and method can be realized.

The present invention will become more fully understood from the detailed description given hereinbelow and the accompanying drawings which are given by way of illustration only, and thus are not to be considered as limiting the present invention.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

FIG. 1 is an explanatory drawing of the pulsed light having passed through the measured object and the output waveform observed by the photodetector having a finite temporal response characteristic.

FIG. 6A and FIG. 6B are explanatory drawings of the operation and the temporal response characteristic between the cathode and the anode in an ordinary photomultiplier tube, respectively.

FIG. 6C and FIG. 6D are explanatory drawings of the operation and the temporal response characteristic between the cathode and the first dynode in an ordinary photomultiplier tube, respectively.

FIG. 6E and FIG. 6F are explanatory drawings of the operation and the temporal response characteristic between the cathode and the anode in a photomultiplier tube according to the present invention, respectively.

FIG. 7 is a timing chart of the operation of the apparatus of the first embodiment.

DESCRIPTION OF THE PREFERRED EMBODIMENTS

The principle of the present invention will be schematically explained prior to the description of the embodiments of the present invention.

Figure 2A:
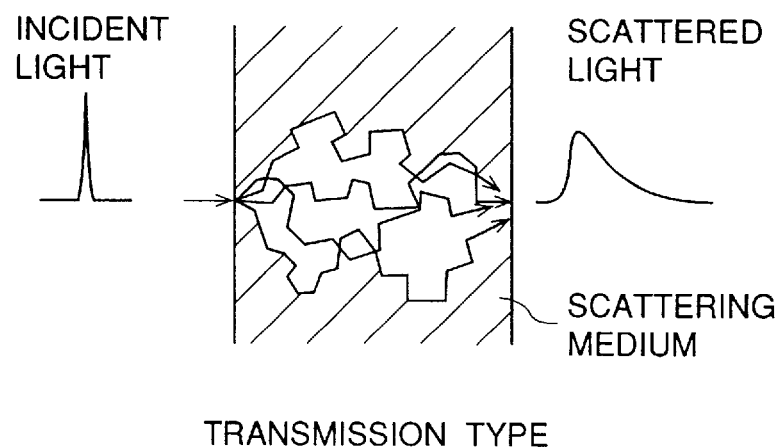
FIG. 2A and FIG. 2B are explanatory drawings of behavior of light inside the scattering medium under a transmission type and a reflection type, respectively.
Figure 2B:
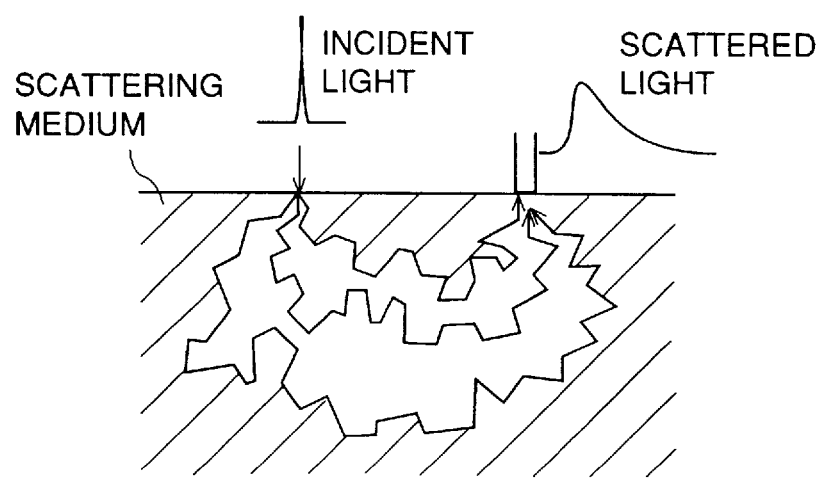

Inside a scattering medium such as the living body, light is subject to scattering and absorption as it diffusely propagates to pass through the inside of the living body and a part thereof comes out of the surface. FIG. 2A and FIG. 2B include explanatory drawings of behavior of the light inside the scattering medium. FIG. 2A shows the behavior in the case of a transmission type while FIG. 2B the behavior in the case of a reflection type. The light incident to the scattering medium spreads throughout the almost entire region in a spherical shape as being irregularly scattered inside, and FIG. 2A and FIG. 2B show trajectories of photons where the light incident at a certain point is detected by the detector set at a place different from the position of incidence. In other words, FIG. 2A and FIG. 2B show the behavior in the scattering medium of the photons actually detected. It is known that such behavior of the light inside the scattering medium can be considerably precisely described by the photon diffusion theory (M. S. Patterson et al., Applied Optics, Vol. 28, No. 12, 15 Jun. 1989, pp 2331–2336) (hereinafter referred to as reference 1)). According to the photon diffusion theory, a light pulse incident to the scattering medium expands its pulse width during diffuse propagation as scattered and absorbed inside the scattering medium. On the other hand, the behavior of individual photons diffusely propagating inside the scattering medium can be analyzed by Monte Carlo simulation using a processing unit. It is also possible to perform experiments actually using a physical model or a living sample of the scattering medium. It is recently confirmed that a result derived from the photon diffusion theory demonstrates good agreement with a result obtained by the Monte Carlo simulation or with a result of the experiment with the physical model. The behavior of the light inside the scattering medium can be accurately described by the photon diffusion theory accordingly.

The photon diffusion theory will be explained. The photon diffusion equation is expressed as follows, for example using the photon fluence rate.

$$\frac{1}{c} \frac{\partial}{\partial t} \phi(r, t) - D\nabla^2\phi(r, t) + \mu_a\phi(r, t) = S(r, t) \quad (1)$$

In the above equation, $\phi(r, t)$: the photon fluence rate [photons/(mm$^2$·sec)] at position r (r: three-dimensional position vector; which is also the same hereinafter) and at time t D: the photon diffusion coefficient [mm]

$\mu_a$: the absorption coefficient [mm$^{-1}$]

c: the velocity of photon in the scattering medium [mm/sec]

S(r, t): the light source [photons/(mm$^3$·sec)]

Since an impulse light source is expressed by a delta function, impulse light incident at the origin (r=0) and at t=0 is expressed as follows.

$$S(r, t) = \delta(r, t) = \delta(0, 0) = \delta(0) \cdot \delta(0)$$

Therefore, the photon diffusion equation for incidence of impulse light is given as follows.

$$\frac{1}{c} \frac{\partial}{\partial t} \phi(r, t) - D\nabla^2\phi(r, t) + \mu_a\phi(r, t) = \delta(0, 0) \quad (2)$$

When the optical constants concerning the scattering medium are defined as follows:

$\mu_s$: the scattering coefficient;

$\mu_s'$: the transport scattering coefficient; and g: the mean cosine of the scattering angle θ, the following relations stand.

$D = [3(\mu_a + \mu_s')]^{-1}$ $\mu_s' = (1-g)\mu_s$

Figure 3:
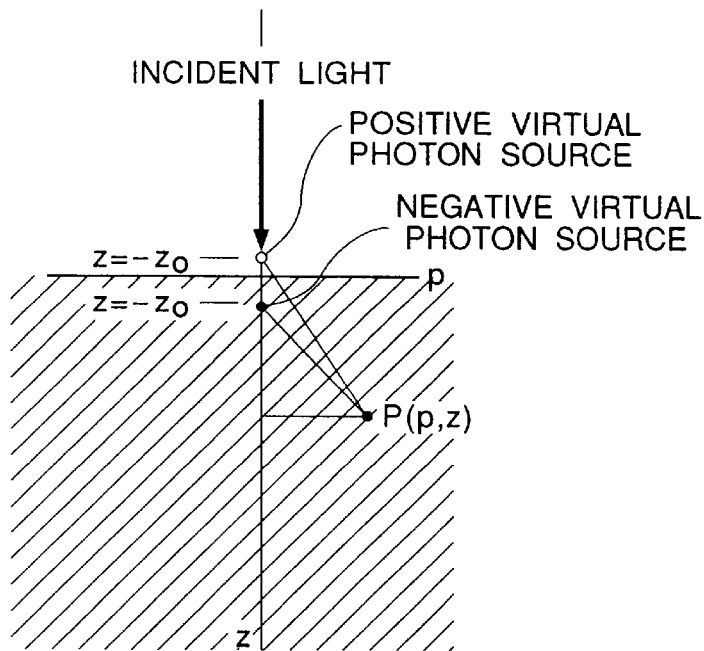
FIG. 3 is an explanatory drawing of positions of virtual photon sources, taking account of the boundary condition of the semi-infinity and slab.

The boundary condition for the case where the light pulse is incident to the scattering medium occupying the half space is realized by placing a negative point light source at the position (ρ=0 (ρ: a two-dimensional position vector; which is also the same hereinafter) and z=−z$_0$), as described in reference 1 and as shown in FIG. 3. Normally, z$_0$ is approximately $1/\mu_s'$. Solving the photon diffusion equation Eq. (2) under this boundary condition, the light signal intensity R(ρ, 0, t) [photons/(mm$^2$·sec)] is obtained as follows at an arbitrary position (ρ, 0) on the surface of the scattering medium.

$$R(\rho, 0, t) = (4\pi Dc)^{-3/2} z_0 t^{-5/2} \times \quad (3)$$
$$\exp[-(z_0^2 + \rho^2)/(4Dct)] \times$$
$$\exp(-\mu_a ct)$$

Then the logarithm of Eq. (3) is differentiated with respect to the time t to obtain a slope at each time of the intensity waveform of the light observed, thereby obtaining Eq. (4).

$$\frac{d}{dt}(\log_e R(\rho, t)) = -\frac{5}{2t} - \mu_a c + \frac{\rho^2}{4Dct} \quad (4)$$

Eq. (5) is obtained by setting $t \to \infty$ in Eq. (4).

$$\lim_{t \to \infty} \frac{d}{dt} (\log_e R(\rho, t)) = -\mu_a c \tag{5}$$

Figure 4:
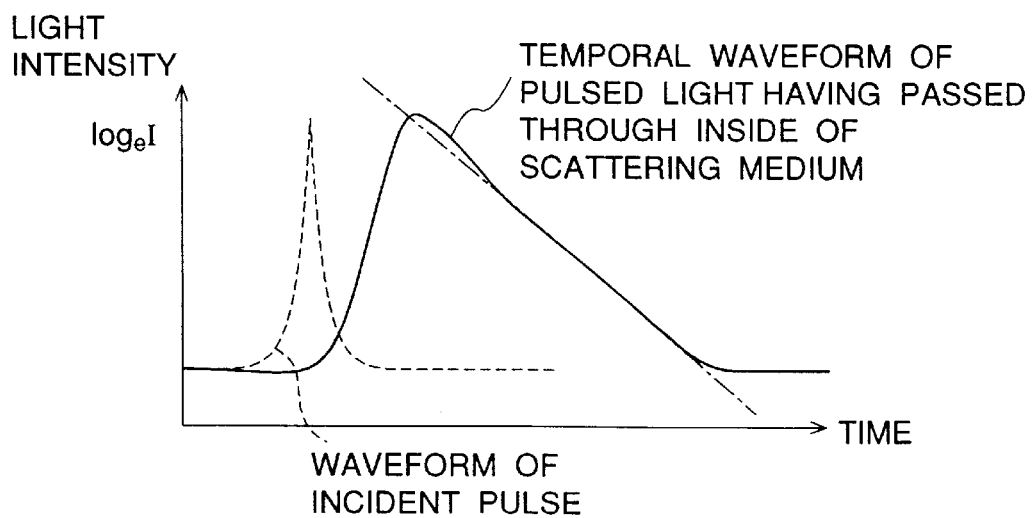
FIG. 4 is a graph to show the relation between the slope of the time-resolved waveform and the absorption coefficient when the pulsed light having passed through the inside of the scattering medium is expressed in a logarithmic form.

Namely, this means that the absorption coefficient can be obtained from a slope of a logarithmic representation of the time-resolved waveform observed at a point when a sufficient time has elapsed after incidence of the pulsed light to the scattering medium. FIG. 4 is an explanatory drawing of a relation of the absorption coefficient with the temporal waveform indicated in the logarithmic form of the pulsed light having passed through the inside of the scattering medium.

Next explained is a method of arithmetic processing for deriving information concerning the absorptive constituent, using the absorption coefficient thus obtained.

[Method for calculating hemoglobin oxygen saturation]

The main absorptive constituents in the brain of mammal are water, cytochrome, and oxygenated and deoxygenated hemoglobin. Absorption of water and cytochrome in the near-infrared region is as small as almost ignorable relative to that of oxygenated and deoxygenated hemoglobin. Thus, let us consider two types of light beams of the wavelength $\lambda_1$ and wavelength $\lambda_2$. Then the absorption coefficients $\mu_{a1}$ and $\mu_{a2}$ for $\lambda_1$ and $\lambda_2$ are given as follows by the Beer-Lambert's law.

$$\mu_{a1} = \epsilon_{11} \cdot [Hb] + \epsilon_{12} \cdot [HbO_2] \tag{6.1}$$

$$\mu_{a2} = \epsilon_{21} \cdot [Hb] + \epsilon_{22} \cdot [HbO_2] \tag{6.2}$$

Here, $\epsilon_{11}$: the molar absorption coefficient $[mm^{-1} \cdot M^{-1}]$ of deoxygenated hemoglobin for the light of frequency=$\lambda_1$ $\epsilon_{12}$: the molar absorption coefficient $[mm^{-1} \cdot M^{-1}]$ of oxygenated hemoglobin for the light of frequency=$\lambda_1$ $\epsilon_{21}$: the molar absorption coefficient $[mm^{-1} \cdot M^{-1}]$ of deoxygenated hemoglobin for the light of frequency=$\lambda_2$ $\epsilon_{22}$: the molar absorption coefficient $[mm^{-1} \cdot M^{-1}]$ of oxygenated hemoglobin for the light of frequency=$\lambda_2$

[Hb]: the molar concentration [M] of deoxygenated hemoglobin

[HbO$_2$]: the molar concentration [M] of oxygenated hemoglobin.

Here, the oxygen saturation Y is defined as follows:

$$Y = [HbO_2]/([HbO_2] + [Hb]) \tag{7}$$

and therefore, the following equation is attained.

$$\frac{\mu_{a1}}{\mu_{a2}} = \frac{(\epsilon_{11} + Y(\epsilon_{12} - \epsilon_{11}))}{(\epsilon_{21} + Y(\epsilon_{22} - \epsilon_{21}))} \tag{8}$$

Therefore, using $\mu_{a1}/\mu_{a2}$ obtained by the aforementioned measurement and the known parameters $\epsilon_{11}$, $\epsilon_{12}$, $\epsilon_{21}$, $\epsilon_{22}$, one can calculate the molar concentration [Hb] of deoxygenated hemoglobin, the molar concentration [HbO$_2$] of oxygenated hemoglobin, the total molar concentration=[Hb]+[HbO$_2$] of hemoglobin, and the oxygen saturation Y (E. M. Sevick et al., Analytical Biochemistry 195, pp 330–351 (1991) (hereinafter referred to as reference 2).

[In the case of background absorption present]

When absorptive constituents other than hemoglobin are dealt with as background absorption, use of a light source of three wavelengths makes more accurate quantitative measurement of hemoglobin concentration possible. In this case, considering the light of the third wavelength=$\lambda_3$ in addition to the light of the two wavelengths ($\lambda_1$, $\lambda_2$), $$\mu_{a1} = \epsilon_{11} \cdot [Hb] + \epsilon_{12} \cdot [HbO_2] + \alpha_1 \tag{9.1}$$

$$\mu_{a2} = \epsilon_{21} \cdot [Hb] + \epsilon_{22} \cdot [HbO_2] + \alpha_2 \tag{9.2}$$

$$\mu_{a3} = \epsilon_{31} \cdot [Hb] + \epsilon_{32} \cdot [HbO_2] + \alpha_3 \tag{9.3}$$

Here, $\alpha_1$: the background absorption $[mm^{-1}]$ of the light of the wavelength=$\lambda_1$ $\alpha_2$: the background absorption $[mm^{-1}]$ of the light of the wavelength=$\lambda_2$ $\alpha_3$: the background absorption $[mm^{-1}]$ of the light of the wavelength=$\lambda_3$ $\epsilon_{31}$: the molar absorption coefficient $[mm^{-1} \cdot M^{-1}]$ of deoxygenated hemoglobin for the light of the wavelength=$\lambda_3$ $\epsilon_{32}$: the molar absorption coefficient $[mm^{-1} \cdot M^{-1}]$ of oxygenated hemoglobin for the light of the wavelength=$\lambda_3$.

Arranging Eqs. (9.1) to (9.3), the following equation is attained.

$$\frac{\mu_{a1} - \mu_{a2}}{\mu_{a3} - \mu_{a2}} = \frac{(\epsilon_{11} - \epsilon_{21}) + Y(\epsilon_{12} - \epsilon_{22} - \epsilon_{11} + \epsilon_{1}) + \frac{(\alpha_1 - \alpha_2)}{(Hbtotal)}}{(\epsilon_{31} - \epsilon_{21}) + Y(\epsilon_{32} - \epsilon_{22} - \epsilon_{31} + \epsilon_{21}) + \frac{\alpha_3 - \alpha_2}{(Hbtotal)}} \tag{10}$$

Here, selecting the wavelengths of light so as to make ($\alpha_1 - \alpha_2$) and ($\alpha_3 - \alpha_2$) sufficiently small, $$\frac{\mu_{a1} - \mu_{a2}}{\mu_{a3} - \mu_{a2}} = \frac{(\epsilon_{11} - \epsilon_{21}) + Y(\epsilon_{12} - \epsilon_{22} - \epsilon_{11} + \epsilon_{21})}{(\epsilon_{31} - \epsilon_{21}) + Y(\epsilon_{32} - \epsilon_{22} - \epsilon_{31} + \epsilon_{21})} \tag{11}$$

the above equation is obtained. Rewriting this into the equation of hemoglobin oxygen saturation Y, $$Y = \left[ (\epsilon_{11} - \epsilon_{21}) \left( \frac{\mu_{a1} - \mu_{a2}}{\mu_{a3} - \mu_{a2}} \right) (\epsilon_{31} - \epsilon_{21}) \right] \div \left[ \left( \frac{\mu_{a1} - \mu_{a2}}{\mu_{a3} - \mu_{a2}} \right) (\epsilon_{32} - \epsilon_{22} - \epsilon_{31} + \epsilon_{21}) - (\epsilon_{12} - \epsilon_{22} - \epsilon_{11} + \epsilon_{21}) \right] \tag{12}$$

the above equation is obtained, and in the same manner as in the above case of the two wavelengths, one can calculate the molar concentration [Hb] of deoxygenated hemoglobin, the molar concentration [HbO$_2$] of oxygenated hemoglobin, the total molar concentration [Hb]+[HbO$_2$] of hemoglobin, and the oxygen saturation Y from the absorption coefficients for the respective beams of the three wavelengths and the known parameters (reference 2).

The embodiments of the apparatus of the present invention will be explained with reference to the accompanying drawings. In the explanation of the drawings, same elements will be denoted by same reference numerals and redundant description will be omitted.

(First embodiment)

Figure 5:
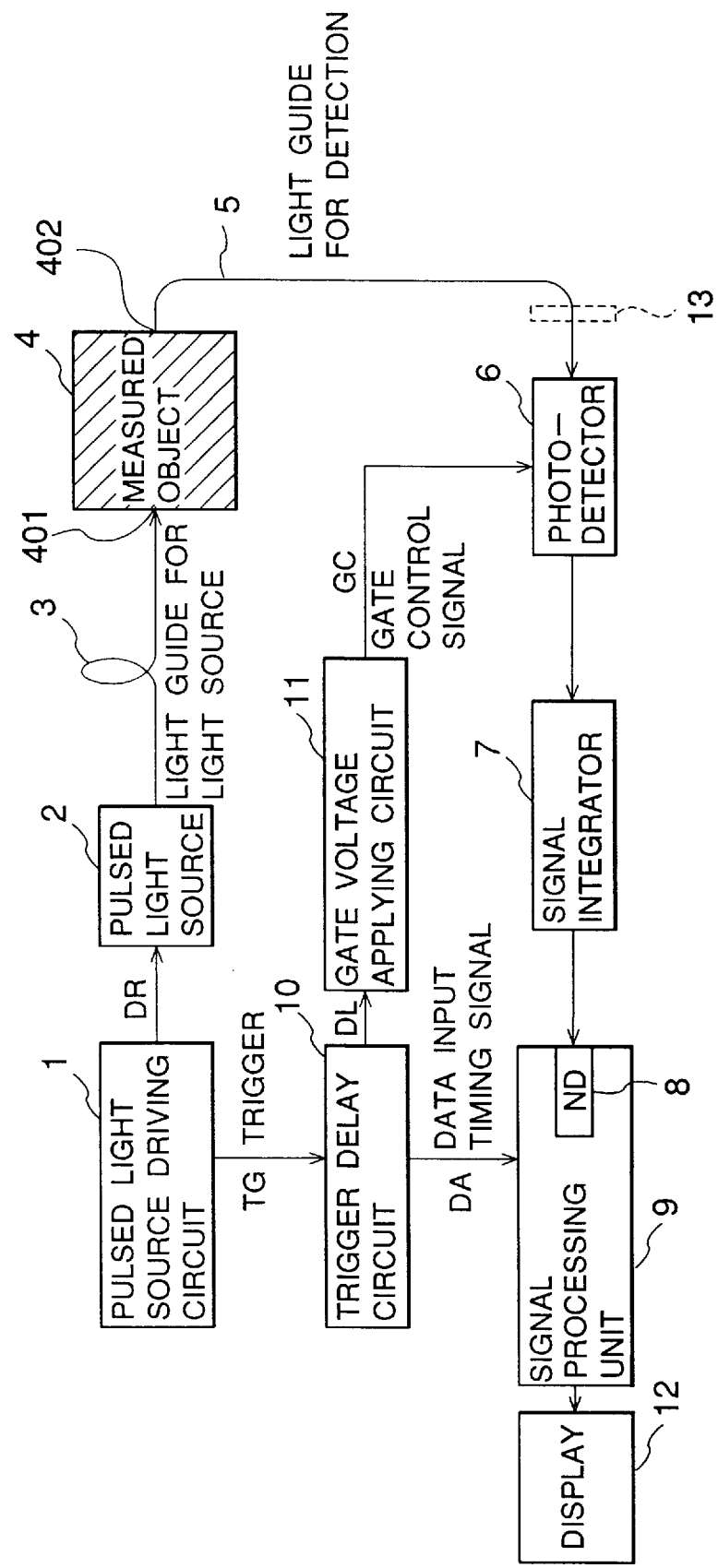
FIG. 5 is a structural drawing of the apparatus of the first embodiment of the present invention.

FIG. 5 is a structural drawing of the first embodiment of the concentration measuring apparatus according to the present invention. As shown in FIG. 5, this apparatus is provided with a pulsed light source driving circuit 1 for pulse-driving the light source, a pulsed light source 2, a light guide 3 for light source arranged to guide pulsed light to a measured object 4, a light guide 5 for detection arranged to guide the pulsed light which has diffusely propagated inside the measured object (a scattering medium) 4 to a photodetector 6, the photodetector 6 for outputting light detection signals according to the intensity of light incident thereto, a signal integrator 7 for integrating signals (signal intensities) detected by the photodetector 6, an A/D converter 8 for converting a signal obtained into a digital signal, a signal processing unit 9 for performing an arithmetic operation with the digital signal and storing a result thereof, a trigger delaying circuit (timing controller) 10 for delaying and adjusting a trigger signal from the pulsed light source driving circuit 1, a gate voltage applying circuit (gate voltage generating circuit) 11 capable of adjusting the pulse width, and a displaying device 12 for displaying a result of the arithmetic operation of the processing unit 9.

In the present embodiment, the photodetector 6 applicable is a photomultiplier tube to a first dynode of which gate voltage pulses (gate signal output) from the gate voltage applying circuit 11 are applied. FIGS. 6A–6F, particularly FIG. 6E and FIG. 6F, are explanatory drawings of the operation of the photodetector 6 constructed in this manner. Specifically, FIG. 6A and FIG. 6B are explanatory drawings of the operation and the temporal response characteristic between the cathode 601' and the anode 602' in an ordinary photomultiplier tube 6', respectively. FIG. 6C and FIG. 6D are explanatory drawings of the operation and the temporal response characteristic between the cathode 601' and the first dynode 611' in an ordinary photomultiplier tube 6', respectively. FIG. 6E and FIG. 6F are explanatory drawings of the operation and the temporal response characteristic between the cathode 601 and the anode 602 in a photomultiplier tube 6 according to the present invention, respectively.

As shown in FIG. 6A and FIG. 6B, the ordinary photomultiplier tubes 6' have the temporal response of several ns between the cathode 601' and the anode 602', but the migration time of electrons is very short, several 100 ps, between the cathode 601' and the first dynode 611' of the photomultiplier tube 6'; as shown in FIG. 6C and FIG. 6D, the temporal response is several 100 ps between the cathode 601' and the first dynode 611'. Therefore, as shown in FIG. 6E and FIG. 6F, application of a gate signal pulse (gate voltage pulse) 621 to the first dynode 611 enables to cut out a part 631 of a waveform reflecting with good repeatability the waveform 632 of the light incident to the cathode 601 at the stage of the first dynode 611. Then the anode 602 outputs a signal (light detection signal) 633 according to the amplitude of the part 631 of the waveform thus cut out times the time.

The waveform of the signal 633 output from the anode 602 can become dull depending upon the time constant between the first dynode 611 and the anode 602 between which dynodes 612–616 are arranged, but a value of time integration of the signal 633 well reflects the amplitude value of the waveform 631 cut out at the stage of the first dynode 611, thus enabling to reproduce the cut-out portion 631 of the incident waveform from the time-integration value of the signal 633 output from the anode 602.

As described, according to the present apparatus comprising the photodetector 6 mentioned above, accurate measurement can be performed with little influence of the temporal response characteristic.

The apparatus of the present embodiment measures a concentration of a specific substance inside the measured object 4 in the following manner. FIG. 7 is a timing chart to explain the operation of the apparatus of the present embodiment.

In the apparatus of the present embodiment, the light output from the pulsed light source 2, such as a laser diode, an LED, an SLD, a mode-locked dye laser, or a titanium sapphire laser, pulse-driven by the pulsed light source driving circuit 1 is guided through the light guide 3 for light source onto the surface of the measured object 4. The wavelength of the light used is properly selected depending upon the measured object. Generally, in the case of the living body is the measured object, the near infrared light ranging from approximately 600 nm to 1500 nm is used because of the absorbance of hemoglobin or the like which depends upon the wavelength.

The pulsed light having diffusely propagated inside the measured object 4 which is a scattering medium is received by the detection light guide 5 located at the position (detection position 402) apart the distance $|\rho|$ from the position (incident position 401) of incidence of light to be guided to the photodetector 6. The photodetector 6 applicable may be an avalanche photodiode or the like in addition to the photomultiplier tube.

If the pulsed light used contains a plurality of wavelengths or if light of the other wavelength than the wavelength of the incident light, for example fluorescence, occurs inside the scattering medium, a wavelength selecting filter 13 may be located between the photodetector 6 and the measured object 4 as occasion demands.

The trigger delaying circuit 10 adjusts the trigger signal (TG) from the pulsed light source driving circuit 1 to the first detection timing ($t_{d1}$) corresponding to a temporal attenuation slope of the intensity of the pulsed light which has diffusely propagated inside the measured object 4, and the first gate voltage pulse ($GC_1$) generated from the gate voltage applying circuit 11 is applied to the photodetector 6, thereby detecting a first light detection signal only during a period ($p_d$) of the first gate voltage pulse applied. The first light detection signal detected by the photodetector 6 is integrated by the signal integrator 7 to be recorded as the first signal intensity ($I_1$) in a memory inside the signal processing unit 9.

Next, the second gate voltage pulse ($GC_2$) is applied to the photodetector 6 at a second detection timing ($t_{d2}$) delayed by an appropriate period of time from the first detection timing ($t_{d1}$) by the trigger delaying circuit 10. The second period ($p_2$) between the incident timing ($t_i$) and the second detection timing ($t_{d2}$) is longer than the first period ($p_1$) between the incident timing ($t_i$) and the first detection timing ($t_{d1}$). Thus, a second light detection signal is detected only during a period ($p_d$) of the second gate voltage pulse ($GC_2$) applied. The second light detection signal detected by the photodetector 6 is integrated by the signal integrator 10 to be recorded as the second signal intensity ($I_2$) in the memory inside the signal processing unit 9.

In the signal processing unit 9, the temporal attenuation slope of the intensity of the pulsed light which has diffusely propagated inside the measured object 4 is calculated from a time difference between the first period ($p_1$) and the second period ($p_2$) and a ratio of the logarithm of the first signal intensity ($I_1$) and the logarithm of the second signal intensity ($I_2$), thereby calculating the absorption coefficient of the inside of the scattering medium as internal information of the scattering medium. The result thus calculated is displayed on the displaying device 12.

Generally, when the living body is irradiated with pulsed light of a very short time width, the attenuation time of the pulse waveform having passed through the inside of the living body, i.e., the period of time between the peak of the light intensity and the signal of zero is approximately 5 to 10 ns. Thus, the width of the gate voltage pulse applied to the photodetector is desirably approximately 1 ns and the time difference between the first period ($p_1$) for applying the first gate voltage pulse ($GC_1$) and the second period ($p_2$) for applying the second gate voltage pulse ($GC_2$) is desirably 3 to 5 ns.

High repetition rate is desired for the pulsed light source 2 in order to permit short-time measurement, but, because the pulse width is broadened to 10 to 20 ns after passage through inside the living body, in the case of the repetition rate being too high, subsequent waveforms will overlap with preceding waveforms, which makes accurate measurement difficult. Thus, the repetition rate of the pulsed light source used is preferably between 5 MHz and 50 MHz.

The foregoing explained the method for calculating the absorption coefficient of the scattering medium from the temporal attenuation slope of the intensity of pulsed light which has diffusely propagated inside the measured object 4, and the same arithmetic operation can be performed utilizing a rising portion of the signal. Further, the same arithmetic operation can be performed by analyzing with Eq. (3) signals of light intensity cut out by gate signals at three or more different timings during the period in which the light detection signal is present.

(Second embodiment)

Figure 8:
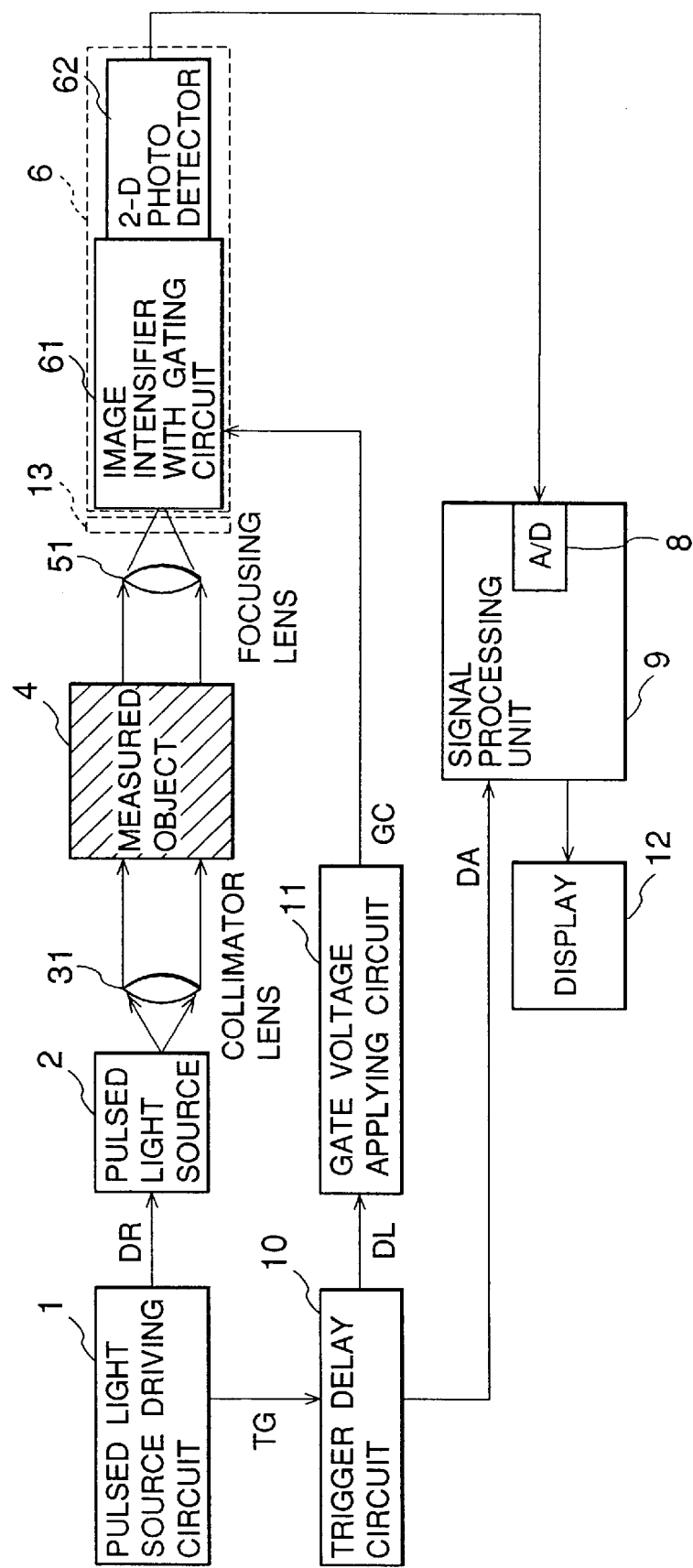
FIG. 8 is a structural drawing of the apparatus of the second embodiment of the present invention.

FIG. 8 is a structural drawing of the second embodiment of the concentration measuring apparatus according to the present invention. As shown in FIG. 8, this apparatus is different from the apparatus of the first embodiment in that it uses a two-dimensional image multiplier 62 having an image intensifier 61 or the like capable of gate-operating as the photodetector 6. The gate voltage pulses are applied at first and second timings, corresponding to the temporal attenuation slope of the intensity of the pulsed light which has diffusely propagated inside the measured object 4, and the temporal attenuation slope of the intensity of the pulsed light is calculated from a ratio of the logarithms of the intensities of the first and second light detection signals obtained during the period of the gate voltage pulse applied, thereby simultaneously calculating one-dimensional or two-dimensional distribution of absorption coefficient inside the scattering medium.

Figure 9:
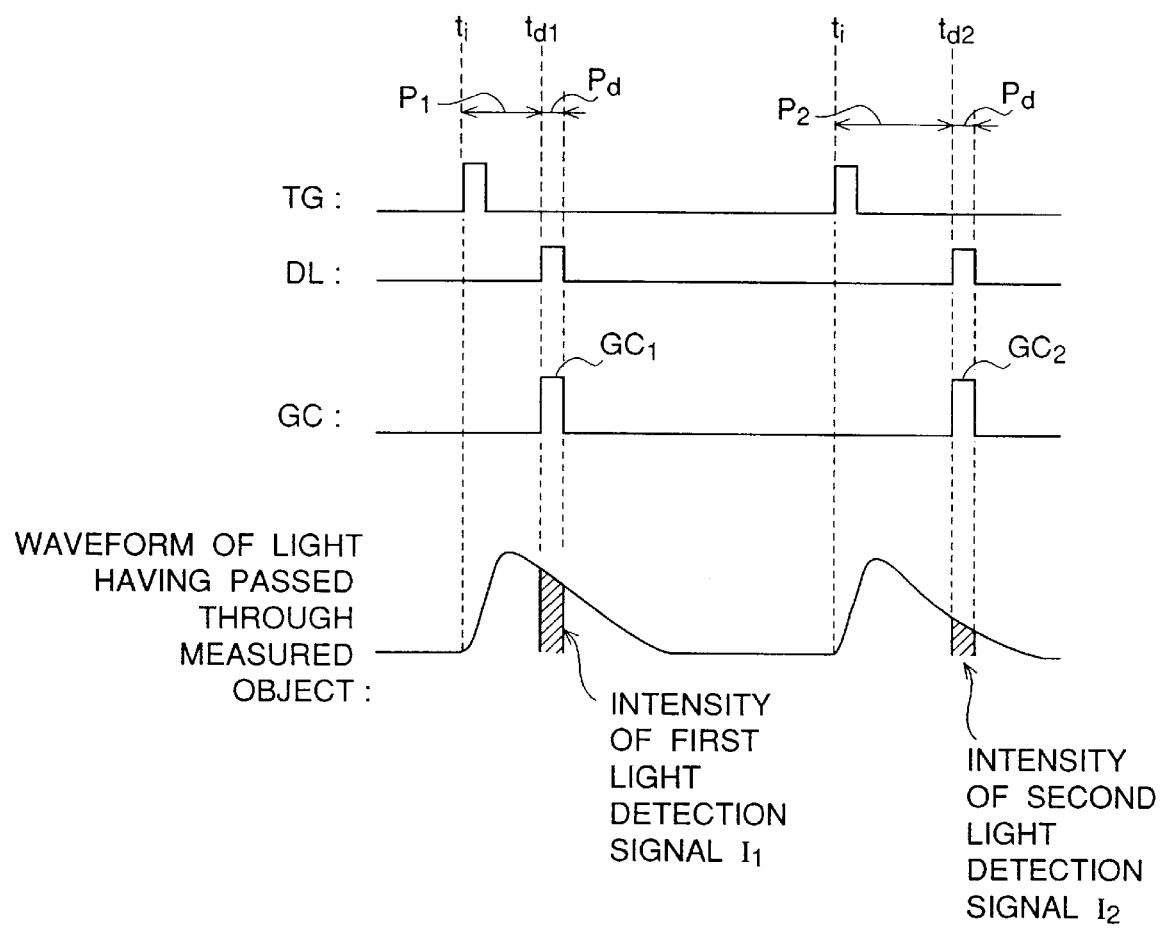
FIG. 9 is a timing chart of the operation of the apparatus of the second embodiment.

The apparatus of the present embodiment measures a concentration of a specific substance inside the measured object 4 in the following manner. FIG. 9 is a timing chart to explain the operation of the apparatus of the present embodiment.

In the apparatus of the present embodiment, a collimator lens 31 collimates a beam from the pulsed light source 2, such as the laser diode, LED, SLD, mode-locked dye laser, or titanium sapphire laser, pulse-driven by the pulsed light source driving circuit 1 to irradiate the measured object 4 therewith. The pulsed light which has diffusely propagated inside the measured object 4 is imaged on the image intensifier 61 with gating circuit by a focusing lens 51.

The trigger delaying circuit (timing controller) 10 adjusts the trigger signal (TG) from the pulsed light source driving circuit 1 to the first detection timing ($t_{d1}$) corresponding to the temporal attenuation slope of the intensity of the pulsed light which has diffusely propagated inside the measured object 4, the first gate voltage pulse ($GC_1$) generated from the gate voltage applying circuit 11 is applied to the image intensifier 61 of the photodetector 6, and the first light detection signal only during the period ($p_d$) of the first gate voltage pulse ($GC_1$) applied is detected as a two-dimensional image by the two-dimensional photodetector 62 such as a CCD camera, connected to the back of the image intensifier 61. The two-dimensional image detected by the two-dimensional detector 62 is converted into a digital signal by the A/D converter 8, which is recorded as an image of the first signal intensity ($I_1$) in the memory inside the processing unit 9.

Next, the second gate voltage pulse ($GC_2$) is applied to the image intensifier 61 at the second detection timing ($t_{d2}$) delayed by an appropriate period of time from the first detection timing ($t_{d1}$) by the trigger delaying circuit 10. The second period ($p_2$) between the incident timing ($t_i$) and the second detection timing ($t_{d2}$) is longer than the first period ($p_1$) between the incident timing ($t_i$) and the first detection timing ($t_{d1}$). Thus, the second light detection signal only during the period ($p_d$) of the gate voltage pulse ($GC_2$) applied is detected as a two-dimensional image by the two-dimensional detector 62. The second two-dimensional image detected by the two-dimensional detector 62 is converted into a digital signal by the A/D converter 8, which is recorded as an image of the second signal intensity ($I_2$) in the memory inside the processing unit 9.

Inside the processing unit 9, the temporal attenuation slope of the intensity of the pulsed light which has diffusely propagated inside the measured object 4 is calculated from the time difference between the first period ($p_1$) and the second period ($p_2$) and a ratio of the logarithm of the first signal intensity ($I_1$) and the logarithm of the second signal intensity ($I_2$) which have been obtained as two-dimensional images, and the two-dimensional distribution of absorption coefficient inside the scattering medium is calculated. Further, the two-dimensional distribution image of absorption coefficient calculated is displayed on the displaying device 12.

Figure 10:
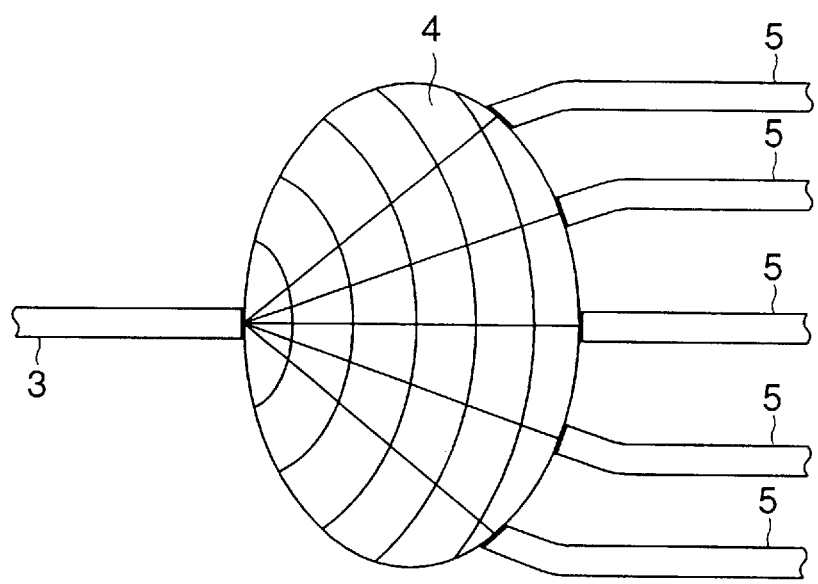
FIG. 10 is a schematic sectional view of an incident position and detection positions of the apparatus of the third embodiment of the present invention.

The pulsed light may be guided to the measured object through a single optical fiber or a plurality of optical fibers. Further, as shown in FIG. 10, a plurality of optical fibers 5 may be set on the surface of the measured object 4 to simultaneously guide a plurality of light detection signals from the surface of the measured object 4 to the image intensifier or the like.

A one-dimensional detector such as a linear diode array may be connected to the back of the image intensifier 61. In this case, the method of signal processing is the same as with the two-dimensional detector such as the CCD, but a calculation result obtained is a one-dimensional distribution of scattering coefficient inside the scattering medium in a direction in which the one-dimensional detector is set. If the pulsed light used includes a plurality of wavelengths or if light of the other wavelength than that of the incident light, for example fluorescence, occurs inside the scattering medium, a wavelength selecting filter 13 may be interposed at an appropriate position between the two-dimensional image multiplier 6 and the measured object 4, if necessary.

The foregoing explained the method for calculating the absorption coefficient of the scattering medium from the temporal attenuation slope of the intensity of the pulsed light which has diffusely propagated inside the measured object 4, but the same arithmetic operation can also be performed utilizing the rising portion of signal. Further, the same arithmetic operation can also be performed by analyzing with Eq. (3) signals of light intensity cut out by gate signals at three or more different timings during the period in which the light detection signal is present.

As detailed above, the apparatus of the present invention is arranged to let the pulsed light of the predetermined wavelength enter the scattering medium such as a living body and to detect the light of the predetermined wavelength coming out of the surface after having diffusely propagated inside the scattering medium, in which a plurality of gate voltage pulses are applied at predetermined timings to the photodetector to cut out plural portions of the output light detection signal and to obtain the time-resolved characteristic of the intensity of the pulsed light which has diffusely propagated. The apparatus of the present invention, therefore, can quantitatively measure from this characteristic internal information of the scattering medium such as a concentration of a specific absorptive constituent inside a living body, for example, the concentration of hemoglobin or the like and the hemoglobin oxygen saturation, at high accuracy and on a noninvasive basis.

From the invention thus described, it will be obvious that the invention may be varied in many ways. Such variations are not to be regarded as a departure from the spirit and scope of the invention, and all such modifications as would be obvious to one skilled in the art are intended to be included within the scope of the following claims.

The basic Japanese Application No.220493/1995 filed on Aug. 29, 1995 is hereby incorporated by reference.

What is claimed is:

1. An apparatus for measuring a scattering medium containing a light absorbing substance, comprising:

a light source for emitting light of a predetermined wavelength at a predetermined incident timing;

a light guide for causing said light to be incident on said scattering medium;

a photodetector, including a photomultiplier tube having a dynode, for detecting intensity of said light which has diffusely propagated through said scattering medium from an incident position to a detection position;

a gate voltage applying circuit for applying gate voltage pulses to said dynode at a plurality of detection timings, periods between said incident timing and said detection timings being different from each other, in order to make said photodetector output light detection signals corresponding to intensity of said light during periods of application of said gate voltage pulses; and a signal processing unit for collecting said light detection signals to obtain signal intensities during the periods of application of said gate voltage pulses, and calculating internal information of said scattering medium based on said signal intensities thus obtained.

2. An apparatus according to claim 1, wherein said photodetector has a gating circuit which is connected to said gate voltage applying circuit.

3. An apparatus according to claim 1, wherein the predetermined wavelength of said light is not less than 600 nm and not more than 1500 nm.

4. An apparatus according to claim 1, wherein said light to be incident on said scattering medium is pulsed light.

5. An apparatus according to claim 1, further comprising a timing controller for controlling said detection timings and said incident timing.

6. An apparatus according to claim 1, wherein said signal processing unit is arranged to obtain a temporal slope of intensity of said light which has diffusely propagated through said scattering medium, based on said signal intensities during the periods of application of said gate voltage pulses, and then to calculate, as said internal information, an absorption coefficient in said scattering medium and a concentration of said absorbing substance based on said temporal slope.

7. An apparatus according to claim 1, wherein said scattering medium contains a plurality of light absorbing substances, said light has a plurality of predetermined wavelengths, and said signal processing unit is arranged to calculate absorption coefficients with respect to said wavelengths and to calculate concentrations of said light absorbing substances based on said absorption coefficients.

8. An apparatus according to claim 1, wherein said scattering medium contains oxygenated hemoglobin and deoxygenated hemoglobin as said light absorbing substance, and said signal processing unit is arranged to calculate a concentration of the oxygenated hemoglobin, a concentration of the deoxygenated hemoglobin and an oxygen saturation of hemoglobin as said internal information.

9. An apparatus according to claim 1, further comprising an integrator for integrating said signal intensities during the periods of application of said gate voltage pulses.

10. An apparatus according to claim 1, wherein said photodetector detects intensity of said light at a plurality of detection positions on the surface of said scattering medium.

11. An apparatus according to claim 1, wherein said dynode is a first dynode of said photomultiplier tube, which has a plurality of dynodes.

12. A method for measuring a scattering medium containing a light absorbing substance, comprising the steps of:

emitting light of a predetermined wavelength from a light source at a predetermined incident timing;

causing said light to be incident on said scattering medium;

detecting intensity of said light by a photodetector, including a photomultiplier tube having a dynode, said light having diffusely propagated through said scattering medium from an incident position to a detection position;

applying gate voltage pulses to said dynode at a plurality of detection timings by a gate voltage applying circuit, periods between said incident timing and said detection timings being different from each other, in order to make said photodetector output light detection signals corresponding to intensity of said light during periods of application of said gate voltage pulses; and collecting said light detection signals by a signal processing unit to obtain signal intensities during the periods of application of said gate voltage pulses, and calculating internal information of said scattering medium based on said signal intensities thus obtained.

13. A method according to claim 12, wherein the steps of detecting intensity and applying gate voltage pulses are carried out with said photodetector having a gating circuit which is connected to said gate voltage applying circuit.

14. A method according to claim 12, wherein the step of emitting light is carried out with said predetermined wavelength of said light being not less than 600 nm and not more than 1500 nm.

15. A method according to claim 12, wherein the step of emitting light is carried out with pulsed light.

16. A method according to claim 12, further comprising the step of:

controlling said detection timings and said incident timing.

17. A method according to claim 12, further comprising the steps of:

obtaining a temporal slope of intensity of said light which has diffusely propagated through said scattering medium, based on said signal intensities during the periods of application of said gate voltage pulses, and calculating, as said internal information, an absorption coefficient in said scattering medium and a concentration of said absorbing substance based on said temporal slope.

18. A method according to claim 12, wherein said scattering medium contains a plurality of light absorbing substances, wherein said light has a plurality of predetermined wavelengths, and further comprising the steps of calculating absorption coefficients with respect to said wavelengths and calculating concentrations of said light absorbing substances based on said absorption coefficients.

19. A method according to claim 12, wherein said scattering medium contains oxygenated hemoglobin and deoxygenated hemoglobin as said light absorbing substance, and further comprising the step of calculating a concentration of the oxygenated hemoglobin, a concentration of the deoxygenated hemoglobin and an oxygen saturation of hemoglobin as said internal information.

20. A method according to claim 12, further comprising the step of integrating said signal intensities during the periods of application of said gate voltage pulses.

21. A method according to claim 12, wherein said detecting of intensity of said light is carried out at a plurality of detection positions on the surface of said scattering medium.

22. A method according to claim 12, wherein the steps of detecting intensity and applying gate voltage pulses are carried out with said dynode being a first dynode of said photomultiplier tube, which has a plurality of dynodes.

23. An apparatus for measuring a scattering medium containing a light absorbing substance, comprising:

a light source for emitting light of a predetermined wavelength at a predetermined incident timing;

a light guide for causing said light to be incident on said scattering medium;

a photodetector for detecting intensity of said light at a plurality of detection positions on a surface of said scattering medium, said light having diffusely propagated through said scattering medium from an incident position to said detection positions;

a gate voltage applying circuit for applying gate voltage pulses to said photodetector at a plurality of detection timings, periods between said incident timing and said detection timings being different from each other, in order to make said photodetector output light detection signals corresponding to intensity of said light during periods of application of said gate voltage pulses; and a signal processing unit for collecting said light detection signals to obtain signal intensities during the periods of application of said gate voltage pulses, and calculating internal information of said scattering medium based on said signal intensities thus obtained.

24. A method for measuring a scattering medium containing a light absorbing substance, comprising the steps of:

emitting light of a predetermined wavelength from a light source at a predetermined incident timing;

causing said light to be incident on said scattering medium;

detecting intensity of said light by a photodetector at a plurality of detection positions on a surface of said scattering medium, said light having diffusely propagated through said scattering medium from an incident position to said detection positions;

applying gate voltage pulses to said photodetector at a plurality of detection timings by a gate voltage applying circuit, periods between said incident timing and said detection timings being different from each other, in order to make said photodetector output light detection signals corresponding to intensity of said light during periods of application of said gate voltage pulses; and collecting said light detection signals by a signal processing unit to obtain signal intensities during the periods of application of said gate voltage pulses, and calculating internal information of said scattering medium based on said signal intensities thus obtained.

* * * * *